United States Patent [19]
Mrowca

[11] 4,257,973
[45] Mar. 24, 1981

[54] PROCESS OF MAKING ACIDS OR ESTERS FROM UNSATURATED COMPOUNDS

[75] Inventor: Joseph J. Mrowca, Wilmington, Del.

[73] Assignee: E. I. Du Pont de Nemours and Company, Wilmington, Del.

[21] Appl. No.: 196,177

[22] Filed: Nov. 5, 1971

[51] Int. Cl.$^3$ ........................ C07C 51/14; C07C 67/38
[52] U.S. Cl. ............................ 260/410.9 R; 260/413; 560/97; 560/114; 560/204; 560/206; 560/232; 560/233; 562/406; 562/497; 562/517; 562/518; 562/519; 562/520; 562/521; 562/522
[58] Field of Search ..... 260/533 AN, 497 B, 486 AC, 260/468 CB, 514 M, 410.9 R, 413, 419 C, 413 C; 560/97, 114, 204, 206, 232, 233; 562/406, 497, 517, 518, 519, 520, 521, 522

[56] References Cited

U.S. PATENT DOCUMENTS

| | | | |
|---|---|---|---|
| 2,739,169 | 3/1956 | Hagenmeyer | 260/540 |
| 2,876,254 | 3/1959 | Jenner et al. | 260/486 |
| 3,437,676 | 4/1969 | von Kutepow et al. | 260/468 |
| 3,455,989 | 7/1969 | von Kutepow et al. | 260/468 |
| 3,661,949 | 5/1972 | Fenton | 260/413 |
| 3,700,706 | 10/1972 | Butter | 260/410.9 R |
| 3,904,672 | 9/1975 | Knifton | 260/410.9 R X |

*Primary Examiner*—Donald G. Daus
*Assistant Examiner*—Diana G. Rivers

[57] ABSTRACT

Water, primary alcohols or secondary alcohols together with carbon monoxide can be added across ethylenic or acetylenic bonds in a wide variety of organic compounds to form acids or esters. The reaction is conducted in the presence of a catalyst system consisting of an organophosphorus palladium halide compound and certain metal halide compounds.

32 Claims, No Drawings

PROCESS OF MAKING ACIDS OR ESTERS FROM UNSATURATED COMPOUNDS

FIELD OF THE INVENTION

This invention relates to a method of making acids and esters from organic compounds containing aliphatic unsaturation. More particularly, this invention relates to a method of making acids and esters by the catalytic addition of hydroxy compounds and carbon monoxide across olefinic or acetylenic unsaturation.

SUMMARY OF THE INVENTION

The process of the present invention is a process for making carboxylic compounds (acids or esters) from aliphatically unsaturated organic compounds by catalytic carboxylation or alkoxycarbonylation by the addition of carbon monoxide and a hydroxy compound, preferably having 1 to 4 primary or secondary hydroxy groups, or water.

The reaction is conducted at a temperature of 35° to 200° C. at a pressure of 1 to 1000 atmospheres in the presence of a catalyst composed of an organophosphorus palladium halide compound and 0.5 to 5 moles per mole of palladium compound of a metallic halide promoter.

The aliphatically unsaturated compounds which are employed as reactants in the practice of this invention are organic compounds having one or more ethylenic or acetylenic groups with the following provisos:

(i) ethylenic groups must have two hydrogen substituents.

(ii) the unsaturated groups are not conjugated with other aliphatic unsaturation (iii) halogen or hydroxyl, if present, must be removed by at least 2 carbon atoms from the unsaturation (iv) the compounds are free of amine groups.

The organophosphorus palladium halide can be represented by the formula $$(PR_3)_2PdXY$$

wherein

X is chlorine or bromine

Y is hydrogen, chlorine, bromine, alkyl of 1 to 5 carbon atoms, aralkyl, acyl of 2 to 4 carbon atoms, or aryl of up to 12 carbon atoms, each R is selected from lower alkyl, cycloalkyl of 3 to 8 carbon atoms, lower alkoxy, aryl of up to 12 carbon atoms, substituted with up to 3 halogen atoms or lower alkoxy groups, aryloxy groups of up to 12 carbon atoms, arylthio of up to 12 carbon atoms, aralkyl of up to 12 carbon atoms, lower alkylthio, di(lower alkyl) amino, pyrrolidino, piperidino and vinyl groups, with the proviso that not more than one aryl group attached to phosphorus contains a substituent in a sterically hindered position.

The promoter is a chloride of Ti, Tl, Ni, Fe, Cr, Mn, Cu, Pd, Zn or Co or a halide compound of Sn.

DETAILED DESCRIPTION OF THE INVENTION

The process of the present invention is a catalyzed addition reaction, carboxylation or alkoxycarbonylation, of water or alcohols and carbon monoxide to aliphatically unsaturated compounds. The reaction is applicable to a wide variety of unsaturated compounds, including compounds with more than one ethylenic and/or acetylenic groups. Difficulty has been experienced where the ethylenic unsaturation is highly branched. Accordingly, two substituents of the olefinic groups should be hydrogen. Hydroxyl or halogen substituents must be removed from the double bond by at least two carbon atoms. Difficulty has also been had with compounds in which two or more aliphatically unsaturated groups are conjugated, or where amine substituents (primary, secondary or tertiary) are present.

Substituents which do not interfere with the reaction of the invention include aryl, lower alkoxy, lower alkoxycarbonyl, carboxyl, lower acyloxy, cyano, carbamoyl, lower acyl and aroyl substituents. Halo and hydroxy substituents can also be present subject to the above noted proviso.

The preferred unsaturated compounds are hydrocarbons or hydrocarbon substituted with the above substituents which hydrocarbon contains at least one group of

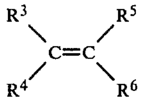, or $R^7-C\equiv C-R^8$, wherein at least two of $R^3$, $R^4$, $R^5$ and $R^6$ are hydrogen, $R^3$ to $R^8$ are hydrogen or aliphatically saturated hydrocarbyl radicals, and any two of $R^3$, $R^4$, $R^5$ and $R^6$ can be joined to form a ring of 3 to 12 carbon atoms.

When more than one unsaturated group is present in the molecule, then at least one of $R^3$ to $R^8$ will be a common, linking radical. Preferably the unsaturated compounds contain up to 30 carbon atoms.

Preferred olefins for the practice of this invention include:

| | |
|---|---|
| Ethylene | Nonadecene-1 |
| Propylene | Docosene-1 |
| Butene-1 | 1,5-Hexadiene |
| Pentene-1 | 1,6-Heptadiene |
| Hexene-1 | 1,7-Octadiene |
| Heptene-1 | 1,8-Nonadiene |
| Octene-1 | 1,9-Decadiene |
| Nonene-1 | 1,10-Undecadiene |
| Decene-1 | 1,11-Dodecadiene |
| Undecene-1 | 4-Vinylcyclohexene |
| Dodecene-1 | Methyl 10-undecenoate |
| Tridecene-1 | Ethyl 10-undecenoate |
| Tetradecene-1 | 10-Undecenoic acid |
| Pentadecene-1 | 10-Undecen-1-ol |
| Hexadecene-1 | 5-Hexen-2-one |
| Heptadecene-1 | 5-Hexenenitrile |
| Octadecene-1 | trans-1,4,9-Decatriene |

Other olefins that can be used in this invention include:

| | |
|---|---|
| Isobutylene | 2,3-Dimethylbutene-1 |
| 2-Methylbutene-1 | 3,3-Dimethylbutene-1 |
| 3-Methylbutene-1 | 2-Methylhexene-1 |
| 2-Methylpentene-1 | 3-Methylhexene-1 |
| 3-Methylpentene-1 | 4-Methylhexene-1 |
| 4-Methylpentene-1 | 5-Methylhexene-1 |
| 3-Ethylpentene-1 | 2,3,3-Trimethylpentene-1 |
| 2,3-Dimethylpentene-1 | 2,3,4-Trimethylpentene-1 |
| 2,4-Dimethylpentene-1 | 2,4,4-Trimethylpentene-1 |
| 3,3-Dimethylpentene-1 | 3,3,4-Trimethylpentene-1 |
| 4,4-Dimethylpentene-1 | 3,4,4-Trimethylpentene-1 |

-continued

| | |
|---|---|
| 2,3,3-Trimethylbutene-1 | 2-Methyloctene-1 |
| 2-Methylheptene-1 | 3-Methyloctene-1 |
| 3-Methylheptene-1 | 7-Methyloctene-1 |
| 4-Methylheptene-1 | 2,6-Dimethylheptene-1 |
| 5-Methylheptene-1 | 3,3-Dimethylheptene-1 |
| 6-Methylheptene-1 | 4,4-Dimethylheptene-1 |
| 3-Ethylhexene-1 | 4-Methyl-4-ethylhexene-1 |
| 4-Ethylhexene-1 | 3,3,5-Trimethylhexene-1 |
| 2,3-Dimethylhexene-1 | 4,4,5-Trimethylhexene-1 |
| 2,4-Dimethylhexene-1 | 2,6-Dimethyloctene-1 |
| 2,5-Dimethylhexene-1 | 3,7-Dimethyloctene-1 |
| 3,3-Dimethylhexene-1 | 2,5,6-Trimethylheptene-1 |
| 3,4-Dimethylhexene-1 | 3,3,6-Trimethylheptene-1 |
| 3,5-Dimethylhexene-1 | 2,3-Dimethyloctene-1 |
| 4,4-Dimethylhexene-1 | 3-Butyloctene-1 |
| 4,5-Dimethylhexene-1 | 3-Propylnonene-1 |
| 5,5-Dimethylhexene-1 | 3,7,11-Trimethyldodecene-1 |
| 2-Methyl-3-ethylpentene-1 | 2-Methylnonadecene-1 |
| 3-Methyl-3-ethylpentene-1 | Eicosene-1 |
| Cyclopentene | Cyclodecene |
| Cyclohexene | Cycloundecene |
| Cycloheptene | Cyclododecene |
| Cyclooctene | Cycloocta-1,5-diene |
| Cyclononene | Butene-2 |
| Pentene-2 | Hexene-2 |
| Hexene-3 | Heptene-2 |
| Octene-2 | Octene-3 |
| Octene-4 | Nonene-2 |
| 4-Methyloctene-2 | 5-Methyloctene-2 |
| 4,6-Dimethyloctene-2 | |
| 4-Methylheptene-2 | 2-Methylhexene-3 |
| 2-Ethylhexene-3 | |

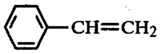
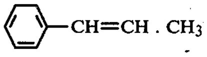
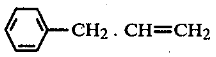
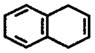
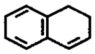
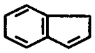
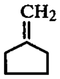
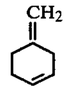
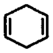
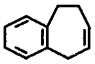
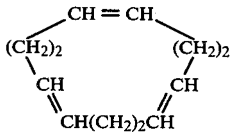

Acetylenic compounds include acetylene, methylacetylene, dimethylacetylene, phenylacetylene, penta-1-yne-4-ene and the like.

Preferred classes include:

(1) 1-alkenes of the formula $CH_3(CH_2)_nCH{=}CH_2$ (2) diolefins of the formula $CH_2{=}CH.(CH_2)_nCH{=}CH_2$ (3) esters of the formula lower alkyl $O.CO.(CH_2)_nCH{=}CH_2$, where n is $<25$.

The alcohols which can be employed in the practice of this invention can be formulated $R^9(OH)_m$ m=1 to 4, preferably 1, and where $R^9$ is a radical of up to 30 carbon atoms derived from a hydrocarbon having at least one aliphatic or alicyclic group and the hydroxy groups are joined to a saturated carbon atom having at least one hydrogen substituent, and removed from aliphatic unsaturation by at least 2 carbon atoms. $R^9$ can also be substituted with the same substituents as $R^3$ to $R^8$.

Preferably the alcohol is a saturated aliphatic monohydric primary or secondary alcohol and most preferably contains up to 10 carbon atoms.

Examples of such alcohols include:

| | |
|---|---|
| Methanol | Hexanol-1 |
| Ethanol | Heptanol-1 |
| Propanol-1 | β-Chloroethanol |
| Propanol-2 | β-Methoxyethanol |
| Pentanol-1 | Benzylalcohol |
| Butanol-1 | Neopentyl alcohol |

Other alcohols that are suitable for this invention include:

| | |
|---|---|
| Isobutyl alcohol | 4,4-Dimethyl-1-pentanol |
| sec-Butyl alcohol | 4,4-Dimethyl-2-pentanol |
| Isoamyl alcohol | 2,2-Dimethyl-3-pentanol |
| 3,3-Dimethyl-1-pentanol | 2-Methylpentan-1-ol |
| 3,3-Dimethyl-2-pentanol | 4-Methylpentan-2-ol |
| 1-Octanol | 2-Methylpentan-3-ol |
| 2-Octanol | 3,3-Dimethylbutan-1-ol |
| 3-Octanol | 3,3-Dimethylbutan-2-ol |
| 4-Octanol | 6-Methyl-1-heptanol |
| 5-Methyl-1-hexanol | 6-Methyl-2-heptanol |
| 5-Methyl-2-hexanol | 6-Methyl-3-heptanol |
| 5-Methyl-3-hexanol | 4-Methyl-3-heptanol |
| 4-Methyl-1-hexanol | 6-Methyl-4-heptanol |
| 4-Methyl-2-hexanol | 5-Methyl-1-heptanol |
| 4-Methyl-3-hexanol | 5-Methyl-2-heptanol |
| 5-Methyl-4-heptanol | 5-Methyl-3-heptanol |
| 2-Methyl-4-heptanol | 5,5-Dimethyl-1-hexanol |
| 4-Methyl-1-heptanol | 5,5-Dimethyl-2-hexanol |
| 4-Methyl-2-heptanol | 5,5-Dimethyl-4-hexanol |
| 3-Methyl-1-heptanol | 1-Nonanol |
| 3-Methyl-2-heptanol | 2-Nonanol |
| 2,2-Dimethyl-1-hexanol | 3-Nonanol |
| 2,2-Dimethyl-3-hexanol | 4-Nonanol |
| 3,3-Dimethyl-1-hexanol | 5-Nonanol |
| 3,3-Dimethyl-2-hexanol | 8-Methyl-1-octanol |
| 4,4-Dimethyl-3-hexanol | 8-Methyl-2-octanol |
| 2,3-Dimethyl-1-hexanol | 7-Methyl-1-octanol |
| 4,5-Dimethyl-1-hexanol | 6-Methyl-1-octanol |
| 4,5-Dimethyl-1-hexanol | 5-Methyl-1-octanol |
| 4,5-Dimethyl-3-hexanol | 2-Methyl-1-octanol |
| 3,5-Dimethyl-1-hexanol | 3-Methyl-1-octanol |
| 3,5-Dimethyl-2-hexanol | 3-Methyl-2-octanol |
| 3,5-Dimethyl-4-hexanol | 1,3-propanediol |

Lauryl alcohols and other dodecanols

| | |
|---|---|
| Tridecanol | 1,4-butanediol |
| Tetradecanol | 1,5-pentanediol |
| Pentadecanol | 1,6-hexanediol |
| Cetyl and other hexadecanols | |
| Oleyl alcohol | Pentaerythritol |
| Heptadecanol | Trimethylolpropane |
| Octadecanol | |
| Nonadecanol | |
| Arachic alcohol or 1-eicosanol | |
| α-Phenethyl alcohol | |
| β-Phenethyl alcohol | |
| 3-Phenylpropanol | |
| 1-Methyl-2-phenylethanol | |
| 4-Phenylbutanol | |
| Cyclopentyl alcohol | |
| Cyclohexyl alcohol | |
| Methylcyclohexyl alcohols | |
| Decanols | |
| Hendecanols | |

-continued

| |
|---|
| 2-Hydroxymethyl-2-methyl-1,3-propanediol |

As noted above, the unsaturated reactant can contain hydroxy groups, and in suitable combination the hydroxy reactant and the unsaturated reactant can be the same. In this case, polyesters are produced by the reaction. The preferred reactants can be represented by the formula $$HO—CH_2.R^{10}.CH=CH_2$$

wherein $R^{10}$ is an aliphatically saturated biradical and preferably a polymethylene chain of 2 to 15 carbon atoms.

The catalyst system employed in the practise of the present invention requires a palladium halide compound complexed with two organophosphorus ligands and a promoter.

The phosphorus ligands have the formula $$PR_3$$

wherein, in general, the $R_3$ groups can be selected from lower alkyl, cycloalkyl of 3 to 8 carbon atoms, lower alkoxy or aryl groups substituted with up to 3 halogen or lower alkoxy groups, aryloxy groups of up to 12 carbon atoms, arylthio of up to 12 carbon atoms, aralkyl, lower alkylthio, di(lower alkyl) amino, pyrrolidino, piperidino or vinyl groups, and can be alike or different, provided that not more than one of the aryl groups has a substituent in a sterically hindered position, i.e., in an adjacent position on the ring system or in the peri position in the naphthalene series.

In the context of this invention, an aryl group is defined as a radical derived from a hydrocarbon containing at least one six-membered aromatic ring by removal of a hydrogen directly attached to a carbon atom of such ring. As thus defined aryl radicals include such species as phenyl groups substituted with lower alkyl groups.

The term "aralkyl" refers to a radical derived from aromatic hydrocarbon having at least one alkyl substituent by removal of an aliphatic hydrogen atom.

The term "lower alkyl" refers to radicals derived from an aliphatic hydrocarbon having from 1 to 6 carbon atoms, by removal of a hydrogen atom.

The term "cycloalkyl" refers to a radical derived from a saturated alicyclic compound by removal of a hydrogen atom.

Examples of suitable ligands include:

| | |
|---|---|
| Triethylphosphine | Diphenyl-N-piperidinylphosphine |
| Tri-n-butylphosphine | Diphenyl-N-pyrrolidinylphosphine |
| Dimethylphenylphosphine | Diphenylbenzylphosphine |
| Diethylphenylphosphine | Methyldiphenylphosphinite |
| Methyldiphenylphosphine | Ethyldiphenylphosphinite |
| Ethyldiphenylphosphine | Phenyldiphenylphosphinite |
| Hexyldiphenylphosphine | Dimethylphenylphosphonite |
| Triphenylphosphine | Diethylphenylphosphonite |
| Tri-p-tolylphosphine | Methyldiphenylthiophosphinite |
| Tri-m-tolylphosphine | Ethyldiphenylthiophosphinite |
| | Phenyldiphenylthiophosphinite |

Other suitable ligands include:

Trimethylphosphine
Triisopropylphosphine
Tri-sec-butylphosphine
Tri-2-methylbutylphosphine
Tripentylphosphine
Triisopentylphosphine
Triheptylphosphine
Dimethylethylphosphine
Methyldiethylphosphine
Diethylisopropylphosphine
Ethyl-t-butylisopropylphosphine
Dipropylbutylphosphine
Tricyclopropylphosphine
Tris(methylcyclopropyl)phosphine
Tricyclohexylphosphine
Dimethyl-p-methoxyphenylphosphine
Dimethyl-p-butylphenylphosphine
Dimethyl-3,4-dimethylphenylphosphine
Dimethyl-2,5-dimethylphenylphosphine
Diethyl-p-methoxyphenylphosphine
Diethyl-p-ethoxyphenylphosphine
Diethyl-p-chlorophenylphosphine
Diethyl-p-bromophenylphosphine
Diethyl-o-tolylphosphine
Diethyl-m-tolylphosphine
Diethyl-p-ethylphenylphosphine
Diethyl-2-methyl-5-isopropylphenylphosphine
Diethyl-2,4,5-trimethylphenylphosphine
Diethyl-1-naphthylphosphine
Dipropylphenylphosphine
Diisopropylphenylphosphine
Diisopropyl-p-methoxyphenylphosphine
Diisopropyl-o-methoxyphenylphosphine
Tri(m-methoxyphenyl)phosphine
Tri(α-naphthyl)phosphine
Tris(4-biphenylyl)phosphine
Diphenyl-p-chlorophenylphosphine
Diphenyl-p-bromophenylphosphine
Diphenyl-p-tolylphosphine
Diphenyl-p-methoxyphenylphosphine
Di-p-tolyl-p-methoxyphenylphosphine
Di-p-tolyl-p-chlorophenylphosphine
Di(p-tolyl)phenylphosphine
Phenyldi(p-bromophenyl)phosphine
Phenyldi(p-chlorophenyl)phosphine
Phenyldi(4-methyl-1-naphthyl)phosphine
Phenyl-p-bromophenyl-p-methoxyphenylphosphine
Phenyl-p-tolyl-p-methoxyphenylphosphine
Diphenyl-2-naphthylphosphine
Phenyldi(1-naphthyl)phosphine
Phenyldi(m-tolyl)phosphine
Phenyldi(3,5-dimethylphenyl)phosphine
Di-p-tolylbenzylphosphine
Isopropyl diphenyl phosphinite
Isobutyl diphenyl phosphinite
Hexyl diphenyl phosphinite
Ethylphenyl p-tolyl phosphinite
Ethyl di(p-tolyl)phosphinite
Ethyl di(p-chlorophenyl)phosphinite
Diisopropyl benzene phosphonite
Diisobutyl benzene phosphonite
Dihexyl benzene phosphonite
Diisopropyl-p-tolylphosphine
Diisopropyl-p-ethylphenylphosphine
Diisopropyl-3,5-dimethylphenylphosphine
Dibutylphenylphosphine
Dibutyl-p-methoxyphenylphosphine
Dibutyl-p-tolylphosphine
Dibutyl-p-ethylphenylphosphine
Dibutyl-2,5-dimethylphenylphosphine
Diisobutylphenylphosphine Diisobutyl-p-tolylphosphine
Diisobutyl-2,5-dimethylphenylphosphine
Dipentylphenylphosphine
Dipentyl-p-methoxyphenylphosphine
Dipentyl-p-tolylphosphine
Dipentyl-p-ethylphenylphosphine
Dipentyl-2,5-dimethylphenylphosphine
Dihexyl-p-chlorophenylphosphine
Di(3-methylbutyl)phenylphosphine
Methyldi-p-tolylphosphine
Methylphenyl-p-tolylphosphine
Ethylphenyl-p-bromophenylphosphine
Ethylphenyl-p-methoxyphenylphosphine
Propylphenyl-p-methoxyphenylphosphine
Butylphenyl-p-methoxyphenylphosphine
Ethylphenyl-p-tolylphosphine
Ethylphenyl-2,4,5-trimethylphenylphosphine
Isopentylphenyl-p-tolylphosphine
Isohexylphenyl-p-tolylphosphine
Heptylphenyl-p-tolylphosphine
Tri(m-chlorophenyl)phosphine
Tri(p-chlorophenyl)phosphine
Diheptyl benzene phosphonite
Diethyl p-toluene phosphonite
Diethyl 2,4,5-trimethylbenzene phosphonite Of the remaining ligands attached to the palladium atom, at least one should be chlorine or bromine. The other ligand can be, in addition to chlorine or bromine, hydrogen, lower alkyl, aralkyl, acyl of 2 to 4 carbon atoms or aryl of up to 12 carbon atoms.

Examples of suitable palladium compounds include:

$[(C_2H_5)_3P]_2PdCl_2$
$[(C_4H_9)_3P]_2PdBr_2$
$[C_6H_5P(C_2H_5)_2]_2PdBrCl$

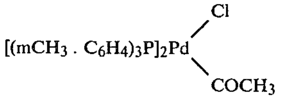

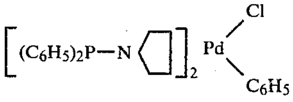

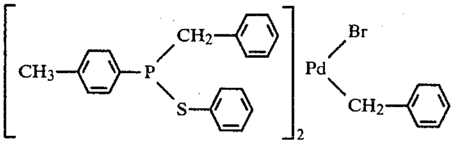

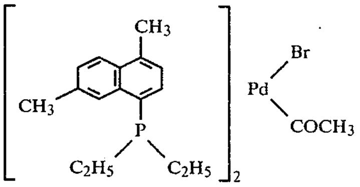

$[(C_6H_5)_3P]_2PdHCl$

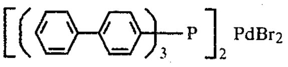

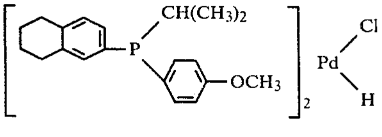

-continued

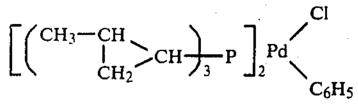

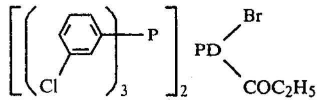

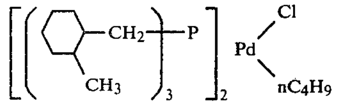

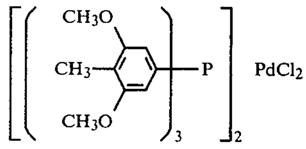

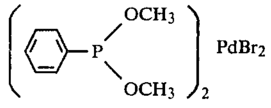

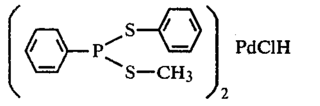

$[(C_6H_5)_2P-CH=CH_2]_2PdCl_2$
$[(C_6H_5-P(OC_2H_5)_2]_2PdCl_2$
$[(C_6H_5)_2P-O-CH(CH_3)_2]_2PdCl_2$

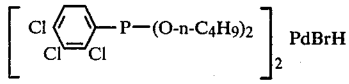

$[(C_2H_5-O)_3P]_2Pd(C_6H_5)Cl$

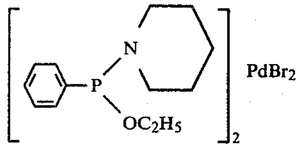

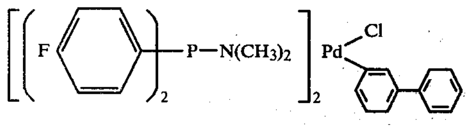

Suitable methods of making palladium complexes for use in the present invention are given by G. Calvin and G. E. Coates, J. Chem. Soc. 1960, 2008, H. Munakata and M. L. H. Green, Chem. Comm. 1970 881, J. M. Jenkins and B. L. Shaw, J. Chem. Soc. (A) 1966, 770, G. Booth and J. Chatt, J. Chem. Soc. (A) 1966, 634, J. M. Jenkins and J. G. Verkode, Inorg. Syn. XI, 108 (1968), K. Kudo, M. Hidai, T. Murayama and Y. Uchida, Chem. Comm. 1970, 1701, G. Booth, Adv. Inorg. Chem. Radiochem., 6, 1 (1964), and in my copending application Ser. No. 189,834, filed Oct. 18, 1971, now U.S. Pat. No. 3,776,929.

The promoter employed with the above palladium compounds are the chlorides of certain metals, namely $TiCl_4$, $TiCl_3$, $NiCl_2$, $CrCl_3$, $MnCl_2$, $FeCl_3$, $FeCl_2$, $PdCl_2$, $CuCl$, $CoCl_2$, $ZnCl_2$ and $TlCl$, or halogen compounds of tin.

The halogen compounds of tin can be $$R^{11}{}_pSnX_{4-p},\ SnXZ,\ \text{or}\ MSnZ_3$$

wherein $R^{11}$ is an aromatic radical of up to 12 carbon atoms consisting of one aryl radical or haloaryl radical, X is chlorine or bromine as defined hereinabove, Z is fluorine, chlorine or bromine, M is a monovalent cation which can be an alkali metal cation or ammonium, p is 0 to 3 inclusive.

Of the halotin compounds, stannous chloride is particularly preferred since it is readily available.

Other preferred tin halide promoters include

| | | |
|---|---|---|
| $SnF_2$ | $SnBr_4$ | $SnBr_2$ |
| $NH_4SnCl_3$ | $SnCl_4$ | |
| $(C_6H_5)_3SnCl$ | $C_6H_5SnCl_3$ | |
| $KSnF_3$ | $KSnCl_3$ | |
| $SnClF$ | $(C_6H_5)_2SnCl_2$ | |

The promoters can be employed as the anhydrous compounds, or in the form of hydrates. In this specification and the the appended claims it is to be understood that the formulae for the promoter compounds includes such modifications as the hydrates.

In general, the promoters are employed in a ratio of 0.5 to 5 moles of promoter per mole of the complex palladium compounds and preferably in about equimolar proportion to the palladium complex compounds.

The promoters increase the conversion of the olefin to acids or esters when reacted with carbon monoxide and water or alcohols respectively in the presence of the aforesaid palladium compounds. The tin halogen compounds have the additional desirable effect of promoting the formation of the linear acid, or ester when the olefin reactant is a terminal olefin.

Temperature

The alkoxycarbonylation and carboxylation of this invention can be effected by heating the olefin, alcohol, or water, organophosphorus palladium catalyst and metal halide promoter in an atmosphere of carbon monoxide at temperatures from 35°–200° C., generally at 50°–150° C., and preferably at 60°–120° C.

Pressure

While carbon monoxide pressures of 1–1000 atmospheres or more can be used in practising this invention, it is preferred to employ pressures in the range of 10–700 atmospheres.

Time

These reactions may be run for as long as 24 hours but 5–10 hour reaction periods generally suffice and are therefore preferred.

Reactors

The process of this invention can be readily carried out using well-known chemical engineering practice which includes continuous, semi-continuous and batch operation.

Reactors used in this invention are not critical as long as they are able to withstand the temperatures and pressures involved. Pressure vessels of high tensile steel are generally used and they may be either lined or unlined. Suitable reactor liners include Hastelloy® metals, stainless steel, silver, aluminum, copper, glass and glazed ceramics.

The reactions are carried out by charging the olefin, if liquid or solid, the alcohol or water, the palladium complex and the metal halide into a suitable pressure-resistant vessel. In cases using water as a reactant, it is sometimes useful to employ a solvent such as acetone, tetrahydrofuran, dioxane, or acetonitrile. For laboratory work, a shaker or rocker system is convenient for agitating the reactants and effecting intimate contact of the reactants. The charged reactor is closed, chilled in Dry Ice, evacuated to remove air, and placed in a shaker or rocker. Olefin, if gaseous, is then added and the system connected to a supply of carbon monoxide and sufficient carbon monoxide added to give the desired pressure at the chosen reaction temperature.

The system is then heated under agitation until reaction is complete. As the reaction proceeds, more carbon monoxide is added periodically to maintain the pressure in the desired range. The course of the reaction is readily followed by observation of the drop in pressure. The product or products can be removed from the reaction mixture by conventional methods of isolation such as distillation.

EMBODIMENTS OF THE INVENTION

The following examples illustrate specific embodiments of the invention. The conversions reported are calculated by the formula:

$$\%\ \text{conversion} = \frac{\text{moles olefin consumed} \times 100}{\text{moles olefin charged}}$$

Similarly the $$\text{“}\%\ \text{linear product”} = \frac{\text{moles linear ester} \times 100}{\text{moles total ester}}$$

The amounts of total ester and linear ester were determined by gas-liquid partition chromatography, abbreviated to chromatography in the examples.

EXAMPLE 1

An 80-cc Hastelloy C lined shaker tube was charged with 20 g (0.238 mol) of 1-hexane, 20 g (0.43 mol) of ethanol, 0.7 g (1 mmol) of dichlorobis(triphenylphosphine)palladium, and 0.23 g (1 mmol) of stannous chloride dihydrate. The mixture was heated at 90° C. under 700 atmospheres of carbon monoxide for 10 hours. A chromatographic analysis of the crude reaction mixture showed that the resulting mixture of esters contained 86.0% of the linear product, ethyl heptanoate. The mixture was evaporated under vacuum, and the residue was distilled to give 20.12 g (0.127 mol, 53.5% yield based on charged 1-hexene) of a mixture of esters which was shown to be mainly ethyl heptanoate by a comparison of its proton nmr spectrum with that of an authentic sample.

EXAMPLE 2

An 80-cc Hastelloy C lined shaker tube was charged with 20 g (0.238 mol) of 1-hexene, 20 g (0.435 mol) of ethanol, 0.56 g (0.8 mmol) of dichlorobis(triphenylphosphine)palladium, and 0.18 g (0.8 mmol) of stannous chloride dihydrate. The mixture was heated at 90° C. under 700 atmospheres of carbon monoxide for 10 hours. A chromatographic analysis of the crude mixture showed an 86% conversion of 1-hexane to a mixture of esters containing 83% of the linear product, ethyl heptanoate. The mixture was evaporated to dryness under vacuum, and the residue was distilled to give 25 g (0.158 mol, 77% yield based on reacted 1-hexene) of esters.

EXAMPLES 3-25

These examples, designed to illustrate the varied complex palladium halides that can be used in catalyzing the alkoxycarbonylation of olefins, follow. The reactor charges had the compositions:

| |
|---|
| 20 g (0.238 mol) of 1-hexene |
| 20 g (0.435 mol) of ethanol |
| (0.8 mmol) $L_2PdCl_2$ (where L is abbreviation for the organophosphorus ligand) |
| 0.18 g (0.8 mmol) $SnCl_2 . 2H_2O$ |

The reaction mixtures were heated at 90° C. under 700 atmospheres of carbon monoxide for 10 hours. The crude reaction mixtures were analyzed as in Examples 1 and 2. The data are summarized in Table I.

TABLE I

| Example | L | % Conversion of 1-Hexene | % Ethyl Heptanoate in Esters |
|---|---|---|---|
| 3 | $(C_6H_5)_2POC_2H_5$ | 36.0 | 80.6 |
| 4(1) | $(C_6H_5)_2PC_2H_5$ | 100.0 | 85.5 |
| 5(2) | $(p-CH_3OC_6H_4)_3P$ | 100.0 | 82.5 |
| 6 | $C_6H_5P(C_2H_5)_2$ | 48.5 | 80.1 |
| 7 | $(m-FC_{64})_3P$ | 15.0 | 70.0 |
| 8 | 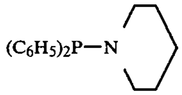 | 19.0 | 84.0 |
| 9 | $(p-FC_6H_4)_3P$ | 84.0 | 68.9 |
| 10 | $(C_6H_5)_2PCH_2C_6H_5$ | 43.0 | 87.0 |
| 11 | $(CH_3)_2PC_6H_5$ | 26.0 | 88.6 |

TABLE I-continued

| Example | L | % Conversion of 1-Hexene | % Ethyl Heptanoate in Esters |
|---|---|---|---|
| 12 | $(C_6H_5)_2PSC_6H_5$ | 30.0 | 82.4 |
| 13(3) | $(C_6H_5)_2PCH_3$ | 57.0 | 83.1 |
| 14 | $o-CH_3C_6H_4P(C_6H_5)_2$ | 2.0 | 69.0 |
| 15 | $(C_2H_5)_3P$ | 9.0 | 73.3 |
| 16 | $o-CH_3C_6H_4P(C_6H_5)_2$(4) | 5.0 | 75.4 |
| 17 | $(C_2H_5)_3P$ | 5.0 | 70.4 |
| 18 | $(p-CH_3C_6H_4)_3P$ | 39.0 | 86.4 |
| 19 | $C_6H_5(C_6H_5CH_2)_2P$ | 2.0 | 63.0 |
| 20 | 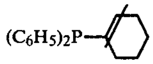 | 99.0 | 71.1 |
| 21 | $(C_2H_5O)_3P$ | 9.0 | 73.0 |
| 22(6,7) | $C_6H_5PdCl[P(C_6H_5)_3]_2$(5) | 12.0 | 90.2 |
| 23(6,8) | $C_6HD_5PdCl[P(C_6H_5)_3]_2$(5) | 92.0 | 84.3 |
| 24(6,8) | $CH_3COPdCl[P(C_6H_5)_3]_2$ | 98.0 | 82.2 |
| 25 | $CH_2=CHP\ (C_6H_5)_2$ | 100.0 | 76.1 |

(1) A parallel experiment run at 80° C. and 50 atmospheres; CO pressure for 10 hours gave 7% conversion to esters of which 84% was ethyl heptanoate.
(2) A parallel experiment run at 70° C. and 50 atmospheres; CO pressure for 10 hours gave 29% conversion to esters of which 87.4% was ethyl heptanoate.
(3) A parallel experiment run at 80° C. and 100 atmospheres; CO pressure for 10 hours gave 19% conversion to esters of which 64.2% was ethyl heptanoate.
(4) mmol + 1.27 mmol $SnCl_2 . 2H_2O$.
(5) Complete formula of Pd complex.
(6) 1 mmol Pd complex and 1 mmol $SnCl_2 . 2H_2O$.
(7) Run at 80° C./100 atmospheres CO.
(8) Run at 90° C./100 atmospheres CO.

EXAMPLES 26-58

The set of Examples in Table II is designed to illustrate the operability of specific metal halide promoters with dichlorobis(triphenylphosphine)palladium. All reactions were run at 90° C. for 10 hours.

TABLE II

| Example | $[(C_6H_5)_3P]_2PdCl_2$ g (mmol) | Metal Halide | g/(mmol) | Pressure Atm. | % Conversion of Hexene | % Ethyl Heptanoate in Ester |
|---|---|---|---|---|---|---|
| 26 | 0.7 (1) | $SnBr_2$ | 0.28 (1) | 700 | 49 | 78.0 |
| 27 | 0.7 (1) | $NH_4SnCl_3$ | 0.24 (1) | 700 | 61 | 86.5 |
| 28 | 0.7 (1) | $SnBr_2 + H_2O$ | 0.28 (1) 3 drops | 700 | 75 | 81.6 |
| 29 | 0.7 (1) | $NH_4SnCl_3$ | 0.24 (1) 3 drops | 100 | 97 | 83.5 |
| 30 | 0.7 (1) | $Ph_3SnCl$ | 0.39 (1) | 100 | 81 | 87.1 |
| 31 | 0.7 (1) | $Ph_3SnCl$ | 0.39 (1) | 100 | 99 | 86.5 |
| 32 | 0.7 (1) | $KSnF_3$ | 0.22 (1) | 700 | 11 | 84.0 |
| 33 | 0.7 (1) | $SnClF + H_2O$ | 0.18 (1) 0.1 g | 700 | 99 | 88.0 |
| 34 | 0.7 (1) | $SnClF$ | 0.18 (1) | 700 | 99 | 86.4 |
| 35 | 0.7 (1) | $PhSnCl_3$ | 0.31 (1) | 700 | 100 | 77.4 |
| 36 | 0.7 (1) | $SnCl_4 . 5H_2O$ | 0.35 (1) | 100 | 95 | 83.1 |
| 37 | 0.7 (1) | $SnF_2$ | 0.32 (2) | 100 | 31 | 82.1 |
| 38 | 0.7 (1) | $SnF_2$ | 0.16 (1) | 700 | 75 | 88.5 |
| 39 | 0.7 (1) | $KSnCl_3 + H_2O$ | 0.27 (1) 3 drops | 100 | 97 | 81.4 |
| 40 | 0.7 (1) | $KSnCl_3$ | 0.27 (1) | 100 | 88 | 79.7 |
| 41 | 0.7 (1) | $SnF_2$ | 0.16 (1) | 700 | 19 | 90.5 |
| 42 | 0.7 (1) | $Ph_2SnCl_2$ | 0.35 (1) | 700 | 99 | 81.7 |
| 43 | 0.7 (1) | $Ph_2SnCl_2$ | 0.35 (1) | 100 | 90 | 84.7 |
| 44 | 0.7 (1) | (none) | — | 700 | 47 | 52.5 |
| 45 | 0.7 (1) | TlCl* | —(1) | 700 | 97 | 60.0 |
| 46 | 0.7 (1) | CuCl | —(1) | 700 | 74 | 42.2 |
| 47 | 0.7 (1) | $PdCl_2$ | —(1) | 700 | 83 | 44.0 |
| 48 | 0.7 (1) | $ZnCl_2$ | —(1) | 700 | 99 | 52.0 |
| 49 | 0.7 (1) | $CoCl_2$ | —(1) | 700 | 70 | 51.2 |
| 50 | 0.7 (1) | $FeCl_2$ | —(1) | 700 | 78 | 56.1 |
| 51 | 0.7 (1) | $TlCl_3 . 4H_2O$ | —(1) | 700 | 89 | 48.0 |
| 52 | 0.7 (1) | $TiCl_3$ | —(1) | 700 | 82.2 | 50.4 |
| 53 | 0.7 (1) | $NiCl_2$ | —(1) | 700 | 58 | 43.0 |
| 54 | 0.7 (1) | $NiCl_2 . 6H_2O$ | —(1) | 700 | 80 | 44.5 |
| 55 | 0.7 (1) | $FeCl_3$ | —(1) | 700 | 80 | 50.0 |
| 56 | 0.7 (1) | $CrCl_3$ | —(1) | 700 | 49 | 52.0 |
| 57 | 0.7 (1) | $CrCl_3 . 6H_2O$ | —(1) | 700 | 59 | 50.0 |

TABLE II-continued

| Example | $[(C_6H_5)_3P]_2PdCl_2$ g (mmol) | Metal Halide g/(mmol) | Pressure Atm. | % Conversion of Hexene | % Ethyl Heptanoate in Ester |
|---|---|---|---|---|---|
| 58 | 0.7 (1) | $MnCl_2 . 4H_2O$ —(1) | 700 | 63 | 53.0 |

*Plus 0.2 g of $H_2O$

EXAMPLES 59–75

These examples form the basis for preferred operating ranges of temperature and pressure.

TABLE III

| Example | $(Ph_3P)_2PdCl_2$ g (mmol) | $SnCl_2 . 2H_2O$ g (mmol) | Temp. (°C.) | Pressure Atm. | Time (Hrs.) | % Conversion 1-Hexene | % Ethyl Heptanoate in Ester |
|---|---|---|---|---|---|---|---|
| 59 | 0.7 (1) | 0.23 (1) | 90 | 50 | 10 | 95 | 87.0 |
| 60 | 0.7 (1) | 0.23 (1) | 90 | 100 | 10 | 100 | 84.5 |
| 61 | 0.7 (1) | 0.23 (1) | 90 | 25 | 10 | 72 | 85.3 |
| 62 | 0.7 (1) | 0.23 (1) | 70 | 50 | 10 | 41 | 89.6 |
| 63 | 0.7 (1) | 0.23 (1) | 80 | 50 | 10 | 84 | 87.5 |
| 64 | 0.7 (1) | 1.15 (5) | 90 | 700 | 10 | 98 | 80.0 |
| 65 | 1.16 (1.6) | 0.36 (1.5) | 70 | 50 | 10 | 54 | 88.9 |
| 66 | 0.7 (1) | 0.46 (2) | 70 | 50 | 10 | 33 | 90.0 |
| 67 | 1.4 (2) | 0.46 (2) | 50 | 100 | 10 | 12 | 87.8 |
| 68 | 0.7 (1) | 0.23 (1) | 80 | 100 | 5 | 62 | 87.2 |
| 69 | 0.7 (1) | 0.23 (1) | 80 | 100 | 10 | 92 | 88.0 |
| 70 | 0.7 (1) | 0.46 (2) | 80 | 100 | 10 | 97 | 85.2 |
| 71 | 0.7 (1) | 0.23 (1) | 90 | 10 | 10 | 27 | 77.8 |
| 72 | 0.7 (1) | 0.23 (1) | 25 | 100 | 10 | 0 | — |
| 73 | 0.7 (1) + 0.2 g $H_2O$ | 0.23 (1) | 80 | 100 | 10 | 99 | 91.4 |
| 74 | 0.7 (1) | 0.23 (1) | 150 | 100 | 10 | 100 | 65.4 |
| 75 | 0.7 (1) | 0.23 (1) | 90 | 100 | 1 | 22 | 79.6 |

These examples were carried out as Example 2 with the exceptions noted in Table III. The reactor was charged with 20 g of 1-hexene, 20 g of ethanol and catalyst as shown in the Table.

EXAMPLES 76–110

The generality of olefins and alcohols that can be employed in this invention is illustrated by the specific embodiments outlined in Table IV.

TABLE IV

| Example | Olefin | mols | Alcohol | mols | $[(C_6H_5)_3P]_2PdCl_2$ g (mmol) | $SnCl_2 . 2H_2O$ g (mmol) | Temp. °C. | Pres. Atm. | Time Hrs. | % Conversion | % Linear Ester |
|---|---|---|---|---|---|---|---|---|---|---|---|
| 76 | 1-Pentene | 0.14 | Neopentyl | 0.28 | 0.7 (1) | 0.23 (1) | 90 | 100 | 10 | 89[(1)] | 86.6 |
| 77 | 2-$CH_3$-1-pentene | 0.24 | Ethyl | 0.48 | 0.7 (1) | 0.23 (1) | 90 | 100 | 10 | 6 | 100 |
| 78 | 5-Hexene-nitrile | 0.11 | Ethyl | 0.48 | 0.7 (1) | 0.23 (1) | 80 | 100 | 10 | 9.6[(1)] | 74 |
| 79 | Ethyl 10-undecenoate | 0.094 | Ethyl | 0.48 | 0.7 (1) | 0.23 (1) | 90 | 100 | 10 | 99.0 | 88[(2)] |
| 80 | 1,9-Decadiene | 0.12 | Ethyl | 0.48 | 0.7 (1) | 0.23 (1) | 90 | 100 | 10 | 100.0 | 68.5[(3)] |
| 81 | 1,9-Decadiene | 0.12 | Ethyl | 0.48 | 0.7 (1) | 0.23 (1) | 70 | 100 | 10 | 75.0 | 73.6[(4)] |
| 82 | 1,9-Decadiene | 0.12 | Ethyl | 0.48 | 1.4 (2) | 0.46 (2) | 70 | 100 | 10 | 100.0 | 79[(5)] |
| 83 | 1,9-Decadiene | 0.12 | Ethyl | 0.48 | 1.4 (2) | 0.46 (2) | 80 | 100 | 10 | 100.0 | 75[(6)] |
| 84 | 1,9-Decadiene | 0.12 | Ethyl | 0.48 | 1.4 (2) | 0.46 (2) | 90 | 100 | 10 | 99 | 70.6[(7)] |
| 85 | 1,9-Decadiene | 0.12 | Methyl | 0.78 | 0.7 (1) | 0.23 (1) | 90 | 700 | 10 | 18 | 66[(8)] |
| 86 | 1,4-Hexadiene | 0.204 | Ethyl | 0.78 | 0.7 (1) | 0.23 (1) | 80 | 100 | 10 | 13 | 100 |
| 87 | 1-Hexene | 0.21 | Isopropyl | 0.38 | 0.61 (0.087) | 0.20 (0.087) | 90 | 700 | 10 | — | 87.8 |
| 88 | 1-Hexene | 0.24 | Methyl | 0.48 | 0.61 (0.087) | 0.20 (0.087) | 90 | 700 | 10 | — | 85.7 |
| 89 | 3-Methyl-1-hexene | 0.25 | Ethyl | 0.54 | 0.7 (1) | 0.23 (1) | 90 | 100 | 10 | 23 | 92.6 |
| 90 | 1-Docosene | 0.12 | Ethyl | 0.48 | 0.7 (1) | 0.23 (1) | 90 | 200 | 10 | — | [(9)] |
| 91 | 10-Hendecen-1-ol | 0.24 | — | — | 0.7 (1) | 0.23 (1) | 80 | 100 | 10 | — | [(10)] |
| 92 | 10-Hendecen-1-ol | 0.12 | Ethyl | 0.25 | 0.7 (1) | 0.23 (1) | 80 | 100 | 10 | — | [(11)] |
| 93 | 4-Vinylcyclohexene | 0.463 | Methyl | 1.56 | 2.1 (3) | 0.68 (1) | 90 | 700 | 15 | — | [(12)] |
| 94 | 5-Hexen-2-one | 0.51 | Ethyl | 1.09 | 1.4 (2) | 0.46 (2) | 80 | 100 | 10 | — | [(13)] |
| 95 | 1,6-Heptadiene | 0.52 | Ethyl | 0.86 | 2.1 (3) | 0.7 (1) | 70 | 100 | 10 | — | [(14)] |
| 96 | 1-Allylcyclohexene | 0.41 | Ethyl | 1.1 | 1.4 (2) | 0.46 (2) | 80 | 100 | 10 | — | [(15)] |
| 97 | 1-Pentene | 0.36 | 1,4-butanediol | 0.133 | 1.05 (1.5) | 0.34 (1.5) | 90 | 100 | 10 | — | [(16)] |
| 98 | 1,8-Nonadiene | 0.4 | Methyl | 1.25 | 1.4 (2) | 0.46 (2) | 70 | 100 | 10 | — | [(17)] |
| 99 | 1-Hexene | 0.18 | Benzyl | 0.32 | 0.7 (1) | 0.23 (1) | 90 | 100 | 10 | — | [(18)] |
| 100 | 1,11-Dodecadiene | 0.3 | Methyl | 1.25 | 1.0 (1.4) | 0.35 (1.5) | 70 | 100 | 10 | 48 | [(19)] |

TABLE IV-continued

| Example | Olefin | mols | Alcohol | mols | $[(C_6H_5)_3P]_2PdCl_2$ g (mmol) | $SnCl_2 \cdot 2H_2O$ g (mmol) | Temp. °C. | Pres. Atm. | Time Hrs. | % Conversion | % Linear Ester |
|---|---|---|---|---|---|---|---|---|---|---|---|
| 101 | 5-Methyl-1-hexene | 0.2 | Ethyl | 0.43 | 0.7 (1) | 0.23 (1) | 90 | 100 | 10 | 89 | 83.4 |
| 102 | 4-Methyl-1-hexene | 0.2 | Ethyl | 0.43 | 0.7 (1) | 0.23 (1) | 90 | 100 | 10 | 92 | 84.5 |
| 103 | 3-Methyl-1-hexene | 0.2 | Ethyl | 0.43 | 0.7 (1) | 0.23 (1) | 90 | 100 | 10 | 98 | 97.3 |
| 104 | 2-Methyl-1-hexene | 0.2 | Ethyl | 0.43 | 0.7 (1) | 0.23 (1) | 90 | 100 | 10 | 6 | 100 |
| 105 | Trans-1,4,9-decatriene | 0.51 | Ethyl | 1.74 | 0.28 (4) | 0.92 (4) | 90 | 100 | 10 | 79 | (20) |
| 106 | 4-Cyanoyclo-hexene | 0.187 | Ethyl | 0.43 | 0.7 (1) | 0.23 (1) | 100 | 200 | 10 | 45 | (21) |
| 107 | Trans-2-hexene | 0.24 | Ethyl | 0.43 | 0.7 (1) | 0.23 (1) | 80 | 100 | 10 | 38 | 9.5(22) |
| 108 | 3-Pentene-nitrile | 0.2 | Ethyl | 0.43 | 0.7 (1) | 0.23 (1) | 100-150 | 100 | 15 | — | (23) |
| 109 | 1-Decyne | 0.36 | Ethyl | 0.87 | 1.4 (2) | 0.46 (2) | 90 | 100 | 10 | 90 | (24) |
| 110 | 1-Pentene | 0.36 | (25) | 0.07 | 0.7 (1) | 0.23 (1) | 90 | 100 | 10 | — | (26) |

(1) By distillation.
(2) Dilinear diester; also 12% other diester.
(3) 88% diesters, 12% monoester; above is dilinear diester.
(4) 38.6% diester; 61.4% monoester; above is dilinear diester.
(5) 81% diester; 19% monoester; above is dilinear diester.
(6) 91% diester; 9% monoester; above is dilinear diester.
(7) 89.9% diester; 10.1% monoester; above is dilinear diester.
(8) % of dilinear diester in diester mixture.
(9) 0.058 mmols (48% yield based on charged olefin) of recrystallized linear ester.
(10) Obtained the polyester $-[O(CH_2)_{11}-\overset{O}{\overset{\|}{C}}]_x-$ containing a small amount of branching ester.
(11) Obtained $HO(CH_2)_{11}-COOC_2H_5$ in 80% yield (0.096 mol) along with a small amount of the branched ester.
(12) Obtained 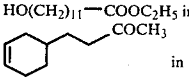 in 43% yield based on charged olefin along with a small amount of the branched ester.
(13) Obtained $CH_3CO(CH_2)_4COOC_2H_5$ in 14% yield based on charged olefin along with a small amount of the branched ester.
(14) Obtained $CH_2{=}CH(CH_2)_5COOEt$ in 52% yield (0.27 mol) containing a small amount of branched ester and $(CH_2)_7(COOCH_3)_3$ in 13% yield (0.067 mol) containing branched diesters. Yields based on charged diolefin.
(15) Obtained 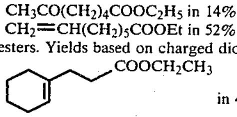 in 43% yield (0.177 mol) containing a small amount of the branched ester. Yield based on charged olefin.
(16) Obtained $CH_3(CH_2)_4COO(CH_2)_4OOC(CH_2)_4CH_3$ in 65% yield (0.086 mol) based on charged 1,4-butanediol.
(17) Obtained $CH_2{=}CH(CH_2)_7COOCH_3$ in 28% yield (0.11 mol) containing a small amount of branched isomer and $(CH_2)_9(COOCH_3)_2$ in 6% yield (0.024 mol) containing branched diesters. Yields based on charged diolefin.
(18) Obtained $CH_3(CH_2)_5COOCH_2C_6H_5$ in 63% yield (0.114 mol) based on charged 1-hexene.
(19) Obtained $CH_2{=}CH(CH_2)_{10}COOCH_3$ in 37% yield (0.053 mol) based on reacted olefin. The diesters were not isolated.
(20) Obtained a 34% yield (0.137 mol) of monoesters based on reacted triolefin. The diesters and triesters were not isolated.
(21) Obtained a 19% yield (0.16 mol) of nitrile-esters based on reacted 4-cyanocyclohexene.
(22) Remainder of esters contained 58.5% $CH_3(CH_2)_3CH(CH_3)COOCH_2CH_3$ and 32% $CH_3(CH_2)_2CH(CH_2CH_3)COOCH_2CH_3$.
(23) Obtained a 5% yield (0.0094 mol) of nitrile-esters based on charged olefin.
(24) Obtained a 52.5% yield (0.172 mol) of $CH_3(CH_2)_7\overset{CH_2}{\overset{\|}{C}}COOCH_2CH_3$ and a 12% yield (0.039 mol) of $CH_3(CH_2)_7CH{=}CHCOOCH_2CH_3$ based on reacted olefin.
(25) 2-Hydroxymethyl-2-methyl-1,3-propanediol.
(26) Obtained a 58% yield (0.0386 mol) of $CH_3C[CH_2O\overset{O}{\overset{\|}{C}}(CH_2)_4CH_3]_3$ containing a small amount of branching. The yield is based on charged triol.

EXAMPLE 111

A mixture of 20 g of 1-hexene, 10 g of water, 10 g of acetone, 0.7 g of dichlorobis(triphenylphosphine)-palladium(II), and 0.23 g of $SnCl_2.2H_2O$ was heated in a shaker tube at 90° C. and 100 atmospheres of carbon monoxide for 10 hours. Volatiles were removed from the reaction mixture under aspirator vacuum, and the residue was mixed with 100 ml of water and extracted twice with ether. The ether extracts were dried over $MgSO_4$ and evaporated to give the crude acid. The acid was analyzed by dissolving a small portion in methanol, adding excess tetramethylammonium hydroxide, and pyrolyzing (300° C.) in a gas chromatograph to give the methyl esters. The gas chromatographic analysis showed that the acid contained 90% of the linear acid, n-heptanoic acid, and 10% of branched isomers. The residue was distilled to give 9 g of product, bp 63°-65° C. at 0.2 mm. The infrared and nmr spectra of the product were identical to those of n-heptanoic acid.

When the procedures detailed in the foregoing examples are applied to the unsaturated compounds of col. 1 and the alcohols of col. 2 in the following table, one obtains the products shown in cols. 3 and 4. In any of the specific alkoxycarbonylations shown, it should be understood that replacement of the alcohol by water and following the procedure of Example 102 leads to the formation of the carboxylic acid corresponding to the ester shown.

| | | | |
|---|---|---|---|
| $CH_2{=}CH_2$ | $CH_3CHOHCH_2CH_3$ | $CH_3CH_2COOCH(CH_3)(C_2H_5)$ | — |
| $CH_3CH{=}CH_2$ | $CH_3(CH_2)_3CH_2OH$ | $CH_3CH_2CH_2COO(CH_2)_4CH_3$ | $(CH_3)_2CHCOO(CH_2)_4CH_3$ |
| $(CH_3)_2CH{=}CH_2$ | $CH_3(CH_2)_5OH$ | $(CH_3)_2CHCH_2COO(CH_2)_5CH_3$ | $(CH_3)_3CCOO(CH_2)_5CH_3$ |
| $CH_3(CH_2)_5CH{=}CH_2$ | $(CH_3)_3CCH_2CH_2OH$ | $CH_3(CH_2)_7COOCH_2CH_2C(CH_3)_3$ | $CH_3(CH_2)_5CHCOOCH_2CH_2C(CH_3)_3$<br>$CH_3$ |
| $CH_3CH_2C{=}CH_2$<br>$CH_3$ | $(CH_3)_2CH(CH_2)_3OH$ | $CH_3CH_2CCH_2COO(CH_2)_3CH(CH_3)_2$<br>$CH_3$ | $CH_3CH_2C(CH_3)_2COO(CH_2)_3CH(CH_3)_2$ |
| $CH_3(CH_2)_7CH{=}CH_2$ | $CH_3(CH_2)_7OH$ | $CH_3(CH_2)_9COO(CH_2)_7CH_3$ | $CH_3(CH_2)_7CHCOO(CH_2)_7CH_3$<br>$CH_3$ |
| $CH_3CH{=}CHCH_3$ | $(CH_3)_3C(CH_2)_3OH$ | $CH_3CHCOO(CH_2)_3C(CH_3)_3$<br>$CH_2CH_3$ | — |
| $CH_3CH_2CH{=}CHCH_3$ | $CH_3(CH_2)_2OH$ | $CH_3(CH_2)_2CHCOO(CH_2)_2CH_3$<br>$CH_3$ | $CH_3CH_2CHCOO(CH_2)_2CH_3$<br>$CH_2CH_3$ |
| $CH_3O(CH_2)_3CH{=}CH_2$ | $NCC_6H_4CH_2OH$ | $CH_3O(CH_2)_5COOCH_2C_6H_4CN$ | $CH_3O(CH_2)_3CHCOOCH_2C_6H_4CN$<br>$CH_3$ |
| 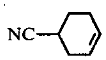 | $CH_3(CH_2)_2CHOH(CH_2)_2CH_3$ | 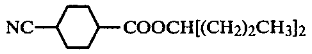 | 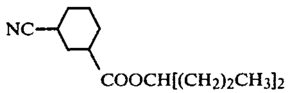 |
| $CH_2{=}CHCH_2C_6H_5$ | $CH_3(CH_2)_{15}OH$ | $C_6H_5(CH_2)_3COO(CH_2)_{15}CH_3$ | $C_6H_5CH_2CHCOO(CH_2)_{15}CH_3$<br>$CH_3$ |
| $CH_3COOCH_2CH{=}CH_2$ | $(CH_3)_2CHCH_2OH$ | $CH_3COO(CH_2)_3COOCH_2CH(CH_3)_2$ | $CH_3COOCH_2CHCOOCH_2CH(CH_3)_2$<br>$CH_3$ |
| $C_2H_5OCOCH_2CH{=}CHCH_3$ | $C_4H_9OH$ | $C_2H_5OCO(CH_2)_2CHCOOC_4H_9$<br>$CH_3$ | $C_2H_5OCOCH_2CHCOOC_4H_9$<br>$CH_2CH_3$ |
| $CH_3COCH_2CH{=}CH_2$ | $CH_3CH_2C(CH_3)_2CH_2OH$ | $CH_3CO(CH_2)_3COOCH_2C(CH_3)_2CH_2CH_3$ | $CH_3COCH_2CHCOOCH_2C(CH_3)_2CH_2CH_3$<br>$CH_3$ |
| $NH_2CO(CH_2)_8CH{=}CH_2$ | $(CH_3)_3C(CH_2)_2OH$ | $H_2NCO(CH_2)_{10}COO(CH_2)_2C(CH_3)_3$ | $H_2NCO(CH_2)_8CHCOO(CH_2)_2C(CH_3)_3$<br>$CH_3$ |
| $CH_3C{\equiv}CH$ | $CH_3(CH_2)_7(CHCl)_2(CH_2)_8OH$ | $CH_3CH{=}CHCOO(CH)_8(CHCl)_2{-}(CH_2)_7CH_3$ | $CH_3CCOO(CH_2)_8(CHCl)_2(CH_2)_7CH_3$<br>$\|\| CH_2$ |
| $C_6H_5COCH_2CH{=}CH_2$ | $C_{10}H_{21}OH$ | $C_6H_5CO(CH_2)_3COOC_{10}H_{21}$ | $C_6H_5COCH_2CHCOOC_{10}H_{21}$<br>$CH_3$ |
| $ClC_6H_4CH_2CH{=}CH_2$ | $(CH_3)_2CHOH$ | $ClC_6H_4(CH_2)_3COOCH(CH_3)_2$ | $ClC_6H_4CH_2CHCOOCH(CH_3)_2$<br>$CH_3$ |
| $CH_3CH_2C{\equiv}CCH_2CH_3$ | $C_6H_5(CH_2)_3OH$ | $CH_3CH_2CH{=}CCOO(CH_2)_3C_6H_5$<br>$CH_2CH_3$ | — |

-continued
| | | | |
|---|---|---|---|
| $C_6H_5C{\equiv}CH$ | $C_4H_9OH$ | 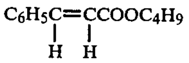 | 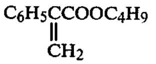 |
| 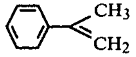 | $CH(CH_3)_2(CH_2)_3OH$ | 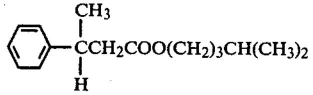 | 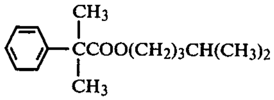 |
| 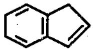 | $C_3H_7OH$ | 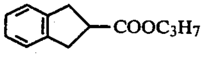 | 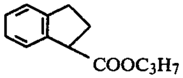 |
| 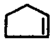 | $C_2H_5OH$ | 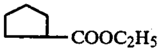 | — |
| 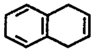 | $CH_3OH$ | 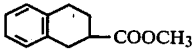 | — |
| 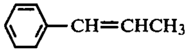 | 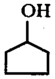 | 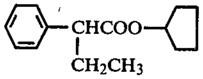 | 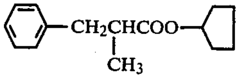 |
| 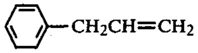 | 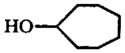 | 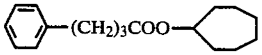 | 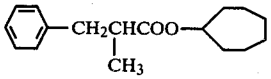 |
| 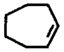 | $C_6H_{13}OH$ | 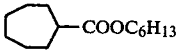 | — |
| 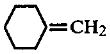 | $C_2H_5OH$ | 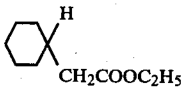 | 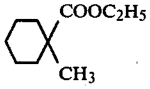 |
| 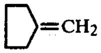 | $CH_3OH$ | 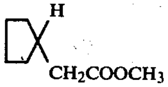 | 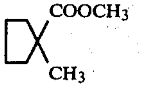 |
| 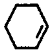 | $CH_3CHOH(CH_2)_4CH_3$ | 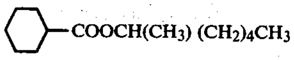 | — |
| 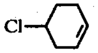 | 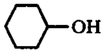 | 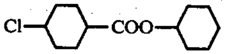 | 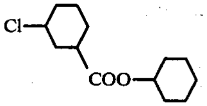 |
| $CH_3OC_6H_4CH{=}CH_2$ | $C_2H_5CHOHC_2H_5$ | $CH_3OC_6H_4CH_2CH_2COOCH(C_2H_5)_2$ | 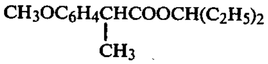 |
| 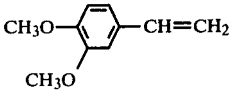 | 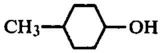 | 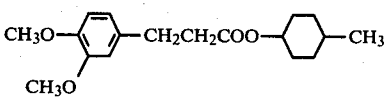 | 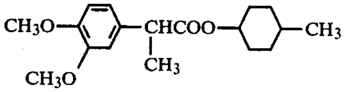 |

-continued

| | | | |
|---|---|---|---|
| $(CH_3)_2NCO(CH_2)_8CH{=}CH_2$ | $C_2H_5OH$ | $(CH_3)_2NCO(CH_2)_{10}COOC_2H_5$ | $(CH_3)_2NCO(CH_2)_8CHCOOC_2H_5$<br>$CH_3$ |
| 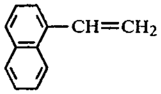 | $C_3H_7OH$ | 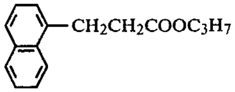 | 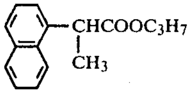 |
| $C_6H_5(CH_2)_2CH{=}CH$ | $C_5H_{11}OH$ | $C_6H_5(CH_2)_2CHCOOC_5H_{11}$<br>$CH_3$ | $C_6H_5(CH_2)_2CHCOOC_5H_{11}$<br>$CH_3$ |
| $CH_3(CH_2)_{12}CH{=}CH$ | $CH_3(CH_2)_3CHOHCH_3$ | $CH_3(CH_2)_{14}COOCH(CH_3)\ (CH_2)_3CH_3$ | $CH_3(CH_2)_{12}CHCOOCH(CH_3)\ (CH_2)_3CH_3$<br>$CH_3$ |
| $C_6H_5CH_2CH{=}CHCH_2C_6H_5$ | $[CH_3(CH_2)_2]_2CHOH$ | $C_6H_5CH_2CHCOOCH[(CH_2)_2CH_3]_2$<br>$CH_2CH_2C_6H_5$ | — |
| 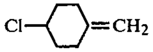 | $HO(CH_2)_2O(CH_2)_2OH$ | 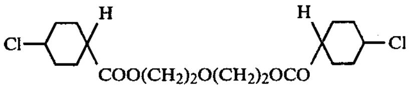 | 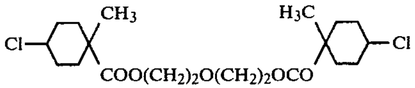<br>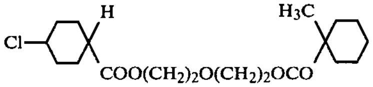 |
| 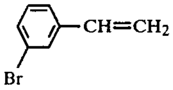 | $C_3H_7OH$ | 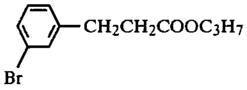 | 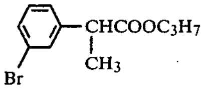 |
| 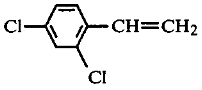 | $C_2H_5OH$ | 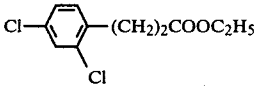 | 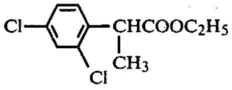 |
| 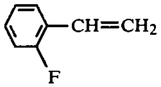 | $CH_3OH$ | 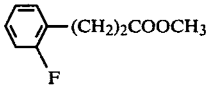 | 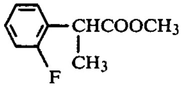 |
| 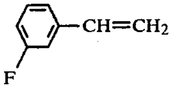 | $CH_3OH$ | 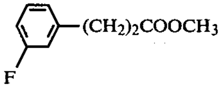 | 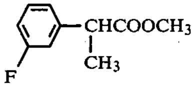 |
| 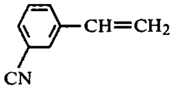 | $CH_3OH$ | 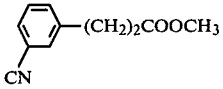 | 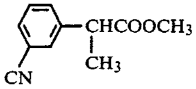 |
| $CH_2{=}CH(CH_2)_2CH{=}CH_2$ | $C_2H_5OH$ | $C_2H_5OCO(CH_2)_6COOC_2H_5$ | $C_2H_5OCO(CH_2)_4CHCOOC_2H_5$<br>$CH_3$ |

-continued

| | | | |
|---|---|---|---|
| | | | $C_2H_5OCOCH(CH_2)_2CHCOOC_2H_5$<br>$\mid \quad \mid$<br>$CH_3 \quad CH_3$ |
| $CH_3C_6H_4CH{=}CH_2$ | $(CH_3)_2CHOH$ | $CH_3C_6H_4(CH_2)_2COOCH(CH_3)_2$ | $CH_3C_6H_4CHCOOCH(CH_3)_2$<br>$\mid$<br>$CH_3$ |
| $CH_3(CH_2)_3CH{=}CH_2$ | $C(CH_2OH)_4$ | $C[CH_2OOC(CH_2)_5CH_3]_4$ | $C[CH_2OOC(CH_2)_5CH_3]_3$<br>$\mid$<br>$CH_2OOCCH(CH_2)_3CH_3$<br>$\mid$<br>$CH_3$ |
| | | $C[CH_2OOC(CH_2)_5CH_3]_2$<br>$\mid$<br>$[CH_2OOCCH(CH_2)_3CH_3]_2$<br>$\mid$<br>$CH_3$ | $CH_3$<br>$C[CH_2OOCCH(CH_2)_3CH_3]_3$<br>$\mid$<br>$CH_2OOC(CH_2)_5CH_3$ |
| 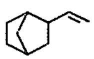 | $CH_3CH_2OH$ | 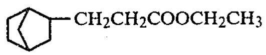 | 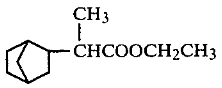 |

Esters are a well-known class of useful organic compounds. Many esters are useful as solvents, and as plasticizers for polymers. Some esters are useful in perfumes, essences, and flavoring agents. Diesters are additionally useful for making polymers, such as polyesters and polyamides. As noted above polyesters can be made directly by the process of the present invention from unsaturated alcohols.

Carboxylic acids which can be made by the process of this invention are also well known to have a variety of uses. Higher molecular weight acids can be used in detergent compositions. Many low molecular weight acids, and particularly salts thereof, are useful as preservatives, as buffering agents, and as solvents. Acids are also extremely important intermediates for the manufacture of ketones, amides, esters, nitriles and many other organic compounds.

The foregoing detailed description has been given for clarity of understanding only and no unnecessary limitations are to be understood therefrom. The invention is not limited to the exact details shown and described for obvious modifications will be apparent to those skilled in the art.

The embodiment of the invention in which an exclusive property or privilege is claimed are defined as follows:

1. A process for making compounds containing carboxylic acid or carboxylic ester groups which comprises reacting an aliphatically unsaturated compound with carbon monoxide and with a hydroxy compound which is water or a primary or a secondary alcohol in the presence of a catalytic amount of a catalyst system composed of a palladium compound having the formula:

$(PR_3)_2PdXY$ wherein

X is chlorine or bromine,

Y is hydrogen, chlorine, bromine, lower alkyl, aralkyl, acyl of 2 to 4 carbon atoms or aryl of up to 12 carbons, and each R is selected from lower alkyl, cycloalkyl of 3 to 8 carbon atoms, lower alkoxy or aryl of up to 12 carbon atoms substituted with up to 3 halogen atoms or lower alkoxy groups, aralkyl groups of up to 12 carbon atoms, arylthio groups or aryloxy groups, each of up to 12 carbon atoms, lower alkylthio, di(lower alkyl)amino, pyrrolidino, piperidino groups and vinyl groups, with the proviso that not more than one aromatic group attached to phosphorus has a substituent in a sterically hindering position, and from 0.5 to 5 moles of a promoter per mole of said palladium compound selected from chlorides of Ti,-Tl,[Ni, Fe,] Cr,[Co,] Pd, Zn, Mn or Cu and halogen tin compounds;

said unsaturated compounds being subject to the following provisos:

(i) ethylenic groups must have at least two hydrogen substituents (ii) the unsaturated groups are not conjugated with other aliphatic unsaturation, (iii) halogen or hydroxyl, if present, must be removed by at least 2 carbon atoms from the double bond, and (iv) the unsaturated compounds are free of amine groups.

2. Process of claim 1 wherein said hydroxylic compound is water.

3. Process of claim 2 wherein said unsaturated compound has at least one group of the formula

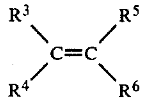 or $R^7-C\equiv C-R^8$ wherein at least two of $R^3$, $R^4$, $R^5$ and $R^6$ are hydrogen, $R^3$ to $R^8$ are aliphatically saturated hydrocarbyl radicals, and any two of $R^3$ to $R^6$ can be joined to form a ring of up to 12 carbon atoms, and when more than one unsaturated group is present in the molecule, at least one of $R^3$ to $R^8$ will be a common linking radical, and said compounds having substituents selected from aryl, lower alkoxy, lower alkoxycarbonyl, lower acyloxy, cyano, carboxyl, carbamoyl, lower acyl, aroyl, halo and hydroxy substituents, said unsaturated compound having up to 30 carbon atoms.

4. Process of claim 3 wherein said unsaturated compound is a terminally unsaturated aliphatic monoolefin.

5. Process of claim 4, wherein said promoter is a halogen-tin compound having the formula $R^{11}{}_pSnX_{4-p}$, SnXZ or $MSnZ_3$ wherein X is chlorine or bromine Z is fluorine, chlorine or bromine, M is an alkali metal cation or ammonium ion, $R^{11}$ is an aromatic radical of up to 12 carbon atoms consisting of aryl radicals or a haloaryl radical p is 0 to 3 inclusive.

6. Process of claim 5 wherein said tin compound is stannous chloride.

7. Process of claim 2 wherein said unsaturated compound is an aliphatic diolefin having two terminal olefin groups.

8. Process of claim 7 wherein said promoter is a halogen-tin compound having the formula $R^{11}{}_pSn_{4-p}$, SnXZ or $MS_nZ_3$ wherein X is chlorine or bromine, Z is fluorine, chlorine or bromine, M is an alkali metal cation or ammonium ion, $R^{11}$ is an aromatic radical of up to 12 carbon atoms consisting of aryl radicals or a haloaryl radical p is 0 to 3 inclusive.

9. Process of claim 8 wherein said tin compound is stannous chloride.

10. Process of claim 1 wherein said alcohol has the formula $R^9(OH)_m$ in which $R^9$ is a radical derived from a hydrocarbon having up to 30 carbon atoms, having at least one aliphatic or alicyclic group, and the hydroxy groups are substituted at a carbon atom bearing at least one other hydrogen and removed by at least two carbon atoms from aliphatic unsaturation, and $m=1$ to 4.

11. Process of claim 10 wherein said unsaturated compound has at least one group of the formula

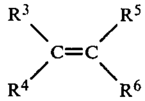

or $R^7—C≡C—R^8$ wherein at least two of $R^3$, $R^4$, $R^5$ and $R^6$ are hydrogen, $R^3$ to $R^8$ are aliphatically saturated hydrocarbyl radicals, and any two of $R^3$ to $R^6$ can be joined to form a ring of up to 12 carbon atoms, and when more than one unsaturated group is present in the molecule, at least one of $R^3$ to $R^8$ will be a common linking radical, and
said compounds having substituents selected from aryl, lower alkoxy, lower alkoxycarbonyl, lower acyloxy, cyano, carboxyl, carbamoyl, lower acyl, aroyl, halo and hydroxy substituents, said unsaturated compound having up to 30 carbon atoms.

12. Process of claim 11 wherein said unsaturated compound is a terminally unsaturated aliphatic monoolefin.

13. Process of claim 12, wherein said promoter is a halogen-tin compound having the formula $R^{11}{}_pSnX_{4-p}$, SnXZ or $MSnZ_3$ wherein
X is chlorine or bromine,
Z is fluorine, chlorine or bromine,
M is an alkali metal cation or ammonium ion,
$R^{11}$ is an aromatic radical of up to 12 carbon atoms consisting of aryl radicals or a haloaryl radical
p is 0 to 3 inclusive.

14. Process of claim 13 wherein said tin compound is stannous chloride.

15. Process of claim 10 wherein said unsaturated compound is an aliphatic diolefin having two terminal olefin groups.

16. Process of claim 15, wherein said promoter is a halogen-tin compound having the formula $R^{11}{}_pSnX_{4-p}$, SnXZ or $MSnZ_3$ wherein
X is chlorine or bromine,
Z is fluorine, chlorine or bromine,
M is an alkali metal cation or ammonium ion,
$R^{11}$ is an aromatic radical of up to 12 carbon atoms consisting of aryl radicals or a haloaryl radical
p is 0 to 3 inclusive.

17. Process of claim 16 wherein said tin compound is stannous chloride.

18. Process of claim 10 wherein said alcohol is a monohydric aliphatic alcohol.

19. Process of claim 18 wherein said unsaturated compound has at least one group of the formula

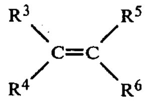

or $R^7—C≡C—R^8$ wherein at least two of $R^3$, $R^4$, $R^5$, and $R^6$ are hydrogen, $R^3$ to $R^8$ are aliphatically saturated hydrocarbyl radical, and any two of $R^3$ to $R^6$ can be joined to form a ring of up to 12 carbon atoms, and when more than one unsaturated group is present in the molecule, at least one of $R^3$ to $R^8$ will be a common linking radical, and
said compounds having substituents selected from aryl, lower alkoxy, loweralkoxy carbonyl, lower acyloxy, cyano, carboxyl, carbamoyl, lower acyl, aroyl, halo and hydroxy substituents, said unsaturated compound having up to 30 carbon atoms.

20. Process of claim 19 wherein said unsaturated compound is a terminally unsaturated aliphatic monoolefin.

21. Process of claim 20, wherein said promoter is a halogen-tin compound having the formula $R^{11}{}_pSn_{4-p}$, SnXZ or $MSnZ_3$ wherein
X is chlorine or bromine,
Z is fluorine, chlorine or bromine,
M is an alkali metal cation or ammonium ion,
$R^{11}$ is an aromatic radical of up to 12 carbon atoms consisting of aryl radicals or a haloaryl radical, and
p is 0 to 3 inclusive.

22. Process of claim 21 wherein said tin compound is stannous chloride.

23. Process of claim 18 wherein said unsaturated compound is an aliphatic diolefin having two terminal olefin groups.

24. Process of claim 23, wherein said promoter is a halogen-tin compound having the formula $R^{11}{}_pSn_{4-p}$, SnXZ or $MSnZ_3$ wherein
X is chlorine or bromine,
Z is fluorine, chlorine or bromine,
M is an alkali metal cation or ammonium ion,
$R^{11}$ is an aromatic radical of up to 12 carbon atoms consisting of aryl radicals or a haloaryl radical, and
p is 0 to 3 inclusive.

25. Process of claim 24 wherein said tin compound is stannous chloride.

26. In a process for the carbonylation of olefinically unsaturated compounds to carbonyl-containing compounds by reacting the olefinically unsaturated hydrocarbon compound with carbon monoxide and with a hydroxylic compound selected from water or a primary or secondary alcohol in the presence of a bis organo phosphine palladium dihalide of the formula $(PR_3)_2PdXY$ where X and Y are chlorine or bromine, and each R is selected from lower alkyl, cycloalkyl of 3 to 8 carbon atoms, aryl of up to 12 carbon atoms substituted with up to 3 halogen atoms or lower alkoxy groups, and aralkyl groups of up to 12 carbon atoms, with the proviso that not more than one aromatic group attached to phosphorus has a substituent in a sterically hindered position, said unsaturated compounds being subject to the following provisos:
(i) ethylenic groups must have at least two hydrogen substituents
(ii) the unsaturated groups are not conjugated with other aliphatic unsaturation
(iii) halogen or hydroxyl, if present, must be removed by at least two carbon atoms from the double bond, and
(iv) the unsaturated compounds are free of amine groups;

the improvement which comprises having a tin co-catalyst or promoter selected from the group consisting of inorganic tin chlorides and triphenyl tin chloride in an amount sufficient to increase the ratio of straight chain to branched chain compounds in the reaction product.

27. A process as defined in claim 26, wherein the temperature is from about 35° C. to about 200° C.

28. A process as defined in claim 26, wherein the hydroxylic compound is an alcohol and the temperature is from about 60° C. to about 120° C.

29. A process as defined in claim 26, wherein the olefinically unsaturated hydrocarbon has from two to 30 carbon atoms.

30. A process as defined in claim 29, wherein the hydroxylic compound is an alcohol and the temperature is from about 60° C. to about 120° C.

31. A process as defined in claim 29, wherein x and y are chlorine.

32. A process as defined in claim 29, wherein the tin co-catalyst or promoter is stannous chloride dihydrate.

* * * * *

UNITED STATES PATENT AND TRADEMARK OFFICE

CERTIFICATE OF CORRECTION

PATENT NO. : 4,257,973

DATED : March 24, 1981

INVENTOR(S) : Joseph J. Mrowca

It is certified that error appears in the above—identified patent and that said Letters Patent is hereby corrected as shown below:

In the Table at Columns 21 and 22:

The third entry in Column 1 should read $C_6H_5(CH_2)_2CH=CH_2$;

The third entry in Column 3 should read $C_6H_5(CH_2)_4COOC_5H_{11}$; and

The fourth entry in Column 1 should read $CH_3(CH_2)_{12}CH=CH_2$;

In Claim 1, Column 25, line 56:

Reference to Ni, Fe, and Co should be deleted.

Signed and Sealed this

Eighth Day of December 1981

[SEAL]

*Attest:*

GERALD J. MOSSINGHOFF

*Attesting Officer* — *Commissioner of Patents and Trademarks*